US009468474B2

(12) United States Patent
Parikh et al.

(10) Patent No.: US 9,468,474 B2
(45) Date of Patent: Oct. 18, 2016

(54) SPINAL DEFORMITY CORRECTION INSTRUMENTS AND METHODS

(71) Applicant: Alphatec Spine, Inc., Carlsbad, CA (US)

(72) Inventors: Anand Parikh, San Mateo, CA (US); Garrett Gleeson, Carlsbad, CA (US); Carmen Walters, Carlsbad, CA (US); Jens Peter Timm, Carlsbad, CA (US); Jonathan Costabile, San Diego, CA (US); Wally Gillespie, Carlsbad, CA (US); Clark Hutton, Oceanside, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 0 days.

(21) Appl. No.: 14/194,258

(22) Filed: Feb. 28, 2014

(65) Prior Publication Data

US 2014/0316475 A1    Oct. 23, 2014

Related U.S. Application Data

(60) Provisional application No. 61/799,009, filed on Mar. 15, 2013, provisional application No. 61/770,897, filed on Feb. 28, 2013.

(51) Int. Cl.
*A61B 17/70* (2006.01)

(52) U.S. Cl.
CPC ......... *A61B 17/7083* (2013.01); *A61B 17/708* (2013.01); *A61B 17/7079* (2013.01); *A61B 17/7086* (2013.01)

(58) Field of Classification Search
CPC ............ A61B 17/7079; A61B 17/708; A61B 17/7083–17/7092
USPC .................................................. 606/86, 86 A
See application file for complete search history.

(56) References Cited

U.S. PATENT DOCUMENTS

| | | | |
|---|---|---|---|
| 8,545,505 B2* | 10/2013 | Sandstrom ......... | A61B 17/7085 606/86 A |
| 2006/0200132 A1* | 9/2006 | Chao et al. ..................... | 606/61 |
| 2007/0213716 A1 | 9/2007 | Lenke et al. | |
| 2008/0077138 A1* | 3/2008 | Cohen et al. .................. | 606/61 |
| 2009/0157125 A1* | 6/2009 | Hoffman et al. ........... | 606/86 A |
| 2010/0249856 A1* | 9/2010 | Iott et al. ..................... | 606/86 A |
| 2011/0087298 A1* | 4/2011 | Jones ................. | A61B 17/7086 606/86 A |
| 2011/0137358 A1 | 6/2011 | Manninen | |
| 2011/0166606 A1 | 7/2011 | Stihl et al. | |
| 2012/0123487 A1 | 5/2012 | Mahar | |
| 2012/0191144 A1* | 7/2012 | Peultier et al. ............. | 606/86 A |
| 2012/0197297 A1* | 8/2012 | Bootwala et al. ............. | 606/246 |
| 2012/0203279 A1* | 8/2012 | Walters et al. ............... | 606/252 |
| 2012/0215315 A1* | 8/2012 | Hochschuler et al. .... | 623/17.16 |
| 2014/0039556 A1* | 2/2014 | Rutschmann et al. ........ | 606/266 |
| 2014/0148865 A1* | 5/2014 | Hennard et al. ............ | 606/86 A |

* cited by examiner

*Primary Examiner* — Jacqueline Johanas
*Assistant Examiner* — Tessa Matthews
(74) *Attorney, Agent, or Firm* — Dinsmore & Shohl LLP

(57) ABSTRACT

An instrument for correction of spinal deformities includes an inner member with a proximal portion configured to receive a corrective force and a distal coupling portion configured to transfer the corrective force to a spinal implant in a vertebra. A slot extends transversely through the coupling portion and is configured to guide a fixation rod into the spinal implant. A threaded sleeve includes an external thread and a thru-bore that slides relative to the proximal portion. An outer member couples with the proximal portion and threadably engages the external thread to apply a reduction force as the outer member rotates relative to the inner member. A reduction blade includes a proximal interlocking portion that removably couples with the threaded sleeve and a distal rod engagement feature configured to engage the fixation rod and transfer the reduction force to reduce the fixation rod into the spinal implant.

20 Claims, 17 Drawing Sheets

SPINAL DEFORMITY CORRECTION INSTRUMENTS AND METHODS

CROSS-REFERENCE TO RELATED APPLICATIONS

The present application claims priority to U.S. Provisional Application Ser. Nos. 61/770,897 which was filed on Feb. 28, 2013 and 61/799,009 which was filed on Mar. 15, 2013, both entitled "Spinal Derotation Systems and Methods" and incorporated herein by reference in their entireties.

FIELD

The invention generally relates to spinal surgery and more particularly to instruments and methods for correcting spinal deformities and reducing spinal rods.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

Spinal fixation systems may be used in surgery to align, adjust, and/or fix portions of the spinal column, i.e., vertebrae, in a desired spatial relationship relative to each other. Many spinal fixation systems employ spinal rods for supporting the spine and for properly positioning components of the spine for various treatment purposes. Vertebral anchors, comprising pins, bolts, screws, and hooks, engage the vertebrae and connect the supporting rod to different vertebrae. The size, length, and shape of the cylindrical rod depend on the size, number, and position of the vertebrae to be held in a desired spatial relationship relative to each other by the apparatus.

During spinal surgery, a surgeon first exposes the spine posterior and attaches the vertebral anchors to selected vertebrae of the spine. The surgeon then inserts a properly shaped spinal rod into rod-receiving portions of the vertebral anchors to connect the selected vertebrae, thereby fixing the relative positions of the vertebrae. Generally, a controlled mechanical force is required to bring together the spinal rod and a spinal implant, such as the vertebral anchors, in a convenient manner. After insertion, a surgeon must insert a locking mechanism, such as a set screw, into the vertebral anchor to lock the spinal rod to the implant after the force for inserting the rod is removed.

The spine is formed in motion segments with each segment represented by two vertebrae and the structures that connect them. The segments allows for six degrees of freedom of movement, resulting in six components of motion for each vertebra V. The movement may be characterized as translation and rotation on each of three axes (X, Y, and Z) forming a Cartesian coordinate system of each vertebra as illustrated in FIG. 1. Each axis is perpendicular to a plane. X is perpendicular to the coronal plane and may be referred to as the coronal axis, Y is perpendicular to the sagittal plane and may be referred to as the sagittal axis, and Z is perpendicular to the transverse plane and may be referred to as the transverse axis.

The axes of each vertebra in a normal standing, static spine, exhibit no rotation in the coronal or transverse planes and a gentle S-shaped curvature in the sagittal plane. In the coronal plane, the vertebrae are normally aligned and present neutral rotation. In the transverse plane, the vertebrae are likewise normally aligned and present neutral rotation. Therefore, the X and Z axes of the different vertebrae are substantially coplanar. In the sagittal plane, the vertebrae present a certain degree of rotation and translation which form the physiological S-shaped curvature: namely, cervical lordosis, thoracic kyphosis, and lumbar lordosis. Therefore, the coronal (X) axes of the thoracic vertebrae are posteriorly divergent in kyphotic segments while they are posteriorly convergent in lordotic segments.

Spinal deformities of varying etiologies which alter the natural alignment of the spine are well known. Such deformities include abnormal spinal curvatures such as scoliosis, kyphosis, and/or other abnormal curvatures. With specific regard to scoliotic deformities, the abnormal curvature of the spinal column is three-dimensional as illustrated in FIG. 2. Specifically, scoliotic deformities can be separated into abnormal translation and/or rotation of the vertebrae in each of the coronal, transverse, and sagittal planes. For example, in a deformed spine, the vertebrae may be rotated and translated in all three planes, as illustrated by arrows R and T, resulting in loss of the normal coplanar alignment of the Y and Z axes. A hypokyphosis may also be present in the thoracic region of the spine causing loss of the normal posterior divergence of X axes. Therefore, treatment of spinal deformities should preferably be aimed at addressing reduction of the abnormal curvature in each of the three spatial planes.

Surgical correction of the rotation and translational alignment of one or more vertebrae in the spinal column typically requires repositioning and re-alignment of the various motion segments. Individual correction of each segment can be time-consuming, cumbersome, and potentially difficult to achieve during a surgical procedure. For example, the alignment of multiple vertebral levels can require manipulation of instrumentation at each level to achieve the desired results. Forces applied to the vertebral body need to be controlled to minimize stresses on the vertebrae and associated implants. Furthermore, alignment at one level often must be maintained while other levels are aligned. Often the instrumentation employed to achieve the alignment can hinder placement of stabilization constructs, such as fixation rods, that post-operatively maintain the corrected positioning and alignment achieved during surgery.

Various individual instruments associated with existing systems and methods may perform individual tasks associated with the following operations: segmental vertebral body alignment, en bloc simultaneous derotation of multiple levels of vertebral bodies, reduction of a fixation rod to an implant head, and stabilization of corrected alignment while setscrews are tightened. These instruments, systems, and methods may facilitate surgical correction of the alignment and positioning of a vertebra or vertebrae of the spinal column, placement of stabilization constructs that post-operatively maintain the corrected vertebra or vertebrae, and facilitate control of the stress exerted on implants and vertebrae to which the implants are attached. However, none of these instruments, systems, and methods is capable of performing all four tasks.

SUMMARY

Accordingly, exemplary instruments, systems, and methods of the present disclosure enable both singular and en bloc derotation and positioning of the vertebrae, sharing of corrective forces across a single vertebra and across one or more motion segments, and application of rod reducing forces to reduce fixation rods.

An instrument for correction of spinal deformities and rod reduction includes an inner member and an outer member. The inner member includes a proximal portion configured to receive a corrective force and a distal coupling portion configured to transfer the corrective force to a spinal implant in a vertebra. A slot extends transversely through the coupling portion and is configured to guide a fixation rod into the spinal implant. A threaded sleeve with an external thread and a thru-bore slides relative to the proximal portion of the inner member. The outer member couples with the proximal portion of the inner member and engages with the external thread to apply a reduction force to the threaded sleeve as the outer member rotates relative to the inner member. A reduction blade includes a proximal interlocking portion that removably couples with the threaded sleeve and a distal rod engagement feature configured to engage the fixation rod and transfer the reduction force to reduce the fixation rod into the spinal implant.

In other features, the instrument includes a second reduction blade including a proximal interlocking portion that removably couples with the threaded sleeve and a distal rod engagement feature configured to engage the fixation rod and transfer the reduction force to reduce the fixation rod into the spinal implant.

In still other features, the instrument includes a guide portion of the inner member aligned with the slot and configured to prevent deflection as the reduction blade applies the reduction force. In other features, the guide portion and the reduction blade engage in a tongue-and-groove configuration. In other features, engagement between the reduction blade and the guide portion prevents rotation of the threaded sleeve relative to the inner member.

In yet other features, the distal coupling portion comprises a locking member including a hinged tab with a projection extending radially inward to engage a recess of the spinal implant.

In yet other features, the instrument includes a mount projecting from the inner member configured to receive a bracket. In other features, the mount includes include one or more ramped portions, a radially extending aperture, and one or more of ridges, beveled edges, a tongue-and-groove, and a T-shaped profile that restricts insertion of the bracket to one direction.

In yet other features, the outer member includes a retainer ring that engages a ridge of the proximal portion to prevent linear translation of the outer member relative to the inner member.

In yet other features, the proximal interlocking portion comprises a T-shaped projection that couples with a mating T-shaped recess of the threaded sleeve.

In yet other features, the instrument is combined with the bracket. The bracket is configured to couple the instrument with a second instrument on an opposite side of the vertebra by a crosslink. In other features, the bracket includes a transverse member extending from the mount and including a pin to engage the mount, a longitudinal member extending from the transverse member at a 90 degree angle, and a rotatable member on an end of the longitudinal member that includes a post to receive the crosslink. In other features, the pin includes a threaded portion and the mount includes a threaded aperture, wherein the pin locks the bracket to the mount by threaded engagement. In other features, the pin includes a spring-loaded pin and the mount includes an aperture, wherein the pin is biased into the aperture to lock the bracket to the mount.

A system for linking two spinal implants inserted in a one vertebra to share corrective forces applied to the vertebra and reduce two rods into the spinal implants includes two instruments, two brackets, and a cross-link.

Each instrument includes an inner member and an outer member. The inner member includes a proximal portion configured to receive a corrective force and a distal coupling portion configured to transfer the corrective force to a spinal implant in a vertebra. A slot extends transversely through the coupling portion and is configured to guide a fixation rod into the spinal implant. A threaded sleeve with an external thread and a thru-bore slides relative to the proximal portion of the inner member. The outer member couples with the proximal portion of the inner member and engages with the external thread to apply a reduction force to the threaded sleeve as the outer member rotates relative to the inner member. A reduction blade includes a proximal interlocking portion that removably couples with the threaded sleeve and a distal rod engagement feature configured to engage the fixation rod and transfer the reduction force to reduce the fixation rod into the spinal implant.

Each bracket includes a transverse member extending from the mount and including a pin to engage the mount, a longitudinal member extending from the transverse member at a 90 degree angle, and a rotatable member on an end of the longitudinal member that includes a post to receive a crosslink.

The cross link couples to each post of the first and second brackets and transfers a portion of the corrective force applied to the first instrument to the second instrument.

A system for linking two spinal implants inserted in two different vertebrae to share corrective forces applied to the vertebrae and reduce a rod into the spinal implants includes two instruments and an alignment clip.

Each instrument includes an inner member and an outer member. The inner member includes a proximal portion configured to receive a corrective force and a distal coupling portion configured to transfer the corrective force to a spinal implant in a vertebra. A slot extends transversely through the coupling portion and is configured to guide a fixation rod into the spinal implant. A threaded sleeve with an external thread and a thru-bore slides relative to the proximal portion of the inner member. The outer member couples with the proximal portion of the inner member and engages with the external thread to apply a reduction force to the threaded sleeve as the outer member rotates relative to the inner member. A reduction blade includes a proximal interlocking portion that removably couples with the threaded sleeve and a distal rod engagement feature configured to engage the fixation rod and transfer the reduction force to reduce the fixation rod into the spinal implant. The alignment clip is configured to couple the first and second instruments to enable en bloc positioning of the vertebrae.

In other features, the alignment clip includes a first arm and a second arm, a hinge portion at a first end that pivotably couples the first arm to the second arm, and a locking portion at a second end that locks the first arm to the second arm. In yet other features, the hinge portion forms a circular portion configured to couple with the outer member of one of the first and second instruments. In yet other features, the locking portion comprises a pin on the first arm, a clasp on the second arm, and a nut to retain the pin in the clasp. In still other features, the first arm and second arm each includes a gripping portion comprising one of a rubber and a silicone-based material to grip one of the first and second instruments.

Each instrument, bracket, cross-link, and alignment clip may be interchangeable with any of the other similar features and components of the systems and methods described herein.

DETAILED DESCRIPTION

The system and method of the present invention includes various features that enable reduction of a fixation rod to an implant head, segmental vertebral body alignment, en bloc simultaneous derotation of multiple levels of vertebral bodies, and stabilization of corrected alignment while setscrews are tightened. The system reduces the complexity of spinal deformity correction procedures and decreases the risk of damage to implants and the vertebral bodies due to high stress concentration at the implant-vertebra interface.

The system comprises a first set of derotation tubes which attaches to the spinal implant heads. A second set of reduction tubes may be inserted over the derotation tubes to reduce a fixation rod to the implant heads. Each reduction tube can accommodate at least 50 mm of reduction. After the reduction of the rod to the implant heads, setscrews may be coaxially inserted to retain the rod to the implant heads. A segmental alignment attachment may be added to each reduction tube. The segmental alignment attachment rotates axially to accommodate the variable lordotic angle of each vertebral body. The reduction tubes may be used to position the segmental alignment attachments vertically. Once all of the segmental alignment attachments are properly positioned, a segmental alignment rod may be inserted to join all segments. A segmental alignment locking knob may then be used to secure each reduction tower to the segmental alignment rod. The setscrews can then be tightened to secure the rods and implants.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 1:
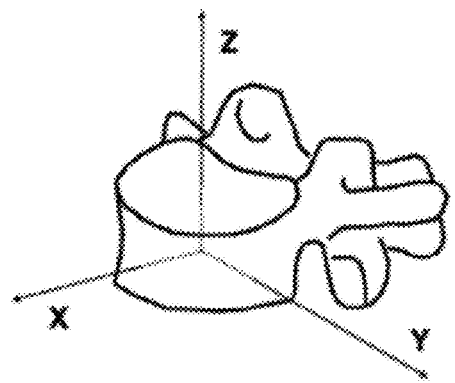
FIG. 1 illustrates an exemplary vertebra and common axes associated with rotational and translation movement.
Figure 2:
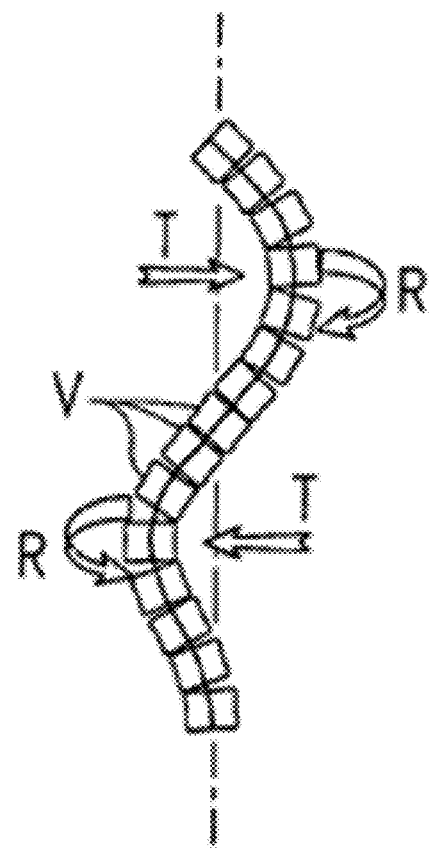
FIG. 2 illustrates an exemplary spinal column exhibiting irregular rotation and translation of the vertebrae.

Referring to FIG. 1, a single vertebra V is shown with reference axes X, Y, and Z. Normally, the vertebrae V are substantially aligned but exhibit some natural curvature in the XZ (sagittal) plane referred to as cervical, thoracic, and lumbar curvature. Generally, no curvature or rotation is present in the YZ (coronal) and XY (transverse) planes. Thus, the X axes, or anteroposterior A-P axes, and the Z axes of normally aligned vertebrae are substantially coplanar. Due to the natural curvature of the spine in the XZ plane, the Y axes of normally aligned vertebrae are not coplanar but are generally parallel. However, in an abnormally deformed spine, such as the scoliotic spine of FIG. 2, vertebral rotation (arrows R) and vertebral translation (arrows T) alter the natural position and alignment of the spine relative to the sagittal, coronal, and transverse planes. The X and Z axes of each vertebra V may no longer be coplanar, and the Y axes of each vertebra V may no longer be parallel. Instruments, systems, and methods of the present disclosure include features to correct deformities of the spinal column and reduce and secure spinal rods within spinal implants.

Figure 3:
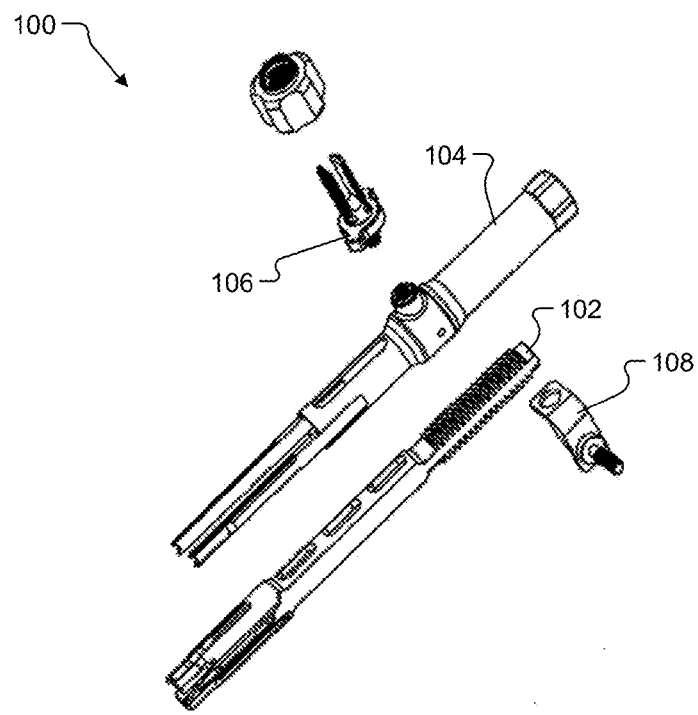
FIG. 3 is an exploded perspective view of an exemplary instrument for derotation, rod reduction, and alignment of the spinal column according to the principles of the present disclosure.
Figure 4:
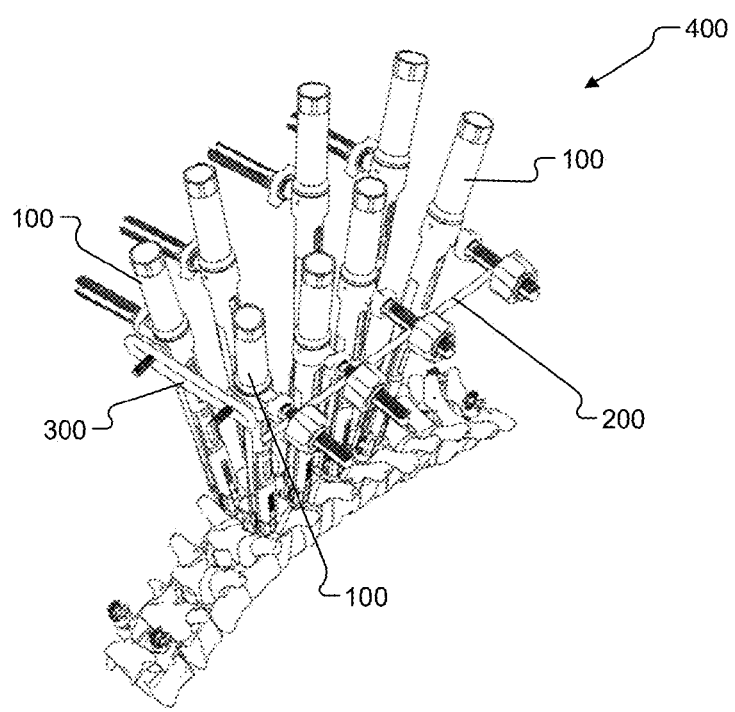
FIG. 4 is a perspective view of an exemplary system for derotation, rod reduction, and alignment of multiple segments of the spinal column according to the principles of the present disclosure.

FIG. 3 illustrates an exploded view of an exemplary derotation and reduction instrument 100 according to the principles of the present disclosure. The instrument 100 includes features that enable repositioning of the vertebrae V through both translational and rotational motion. One or more instruments 100 may attach to opposite sides of the vertebrae V as shown in FIG. 4 via various implants such as one or more pedicle screws. Multiple instruments 100 may be used in conjunction with an alignment rod 200 and a cross-link member 300 in a spinal derotation and alignment system 400 described in further detail below.

Continuing with FIG. 3, the instrument 100 includes a first inner member 102 and a second outer member 104. The inner member 102 may be referred to as a derotation tube and may be used to translate and rotate the vertebra V relative to the X, Y, and Z axes. The outer member 104 may be referred to as a reducer tube and may be used to reduce a fixation rod in a rod receiving head of the spinal implant (not shown). The instrument 100 may further include a segmental alignment coupler 106 for linking multiple instruments 100 together along the length of the spine with the alignment rod 200 as shown in FIG. 4. The instrument 100 may include a cross-link coupler 108 for linking instruments 100 across a single vertebra V with the cross-link member 300 to distribute stress associated with the translational and rotational forces across two or more implant-vertebra interfaces. One or more knobs 110 may be used to couple additional elements to the couplers 106 and/or 108.

Figure 5:
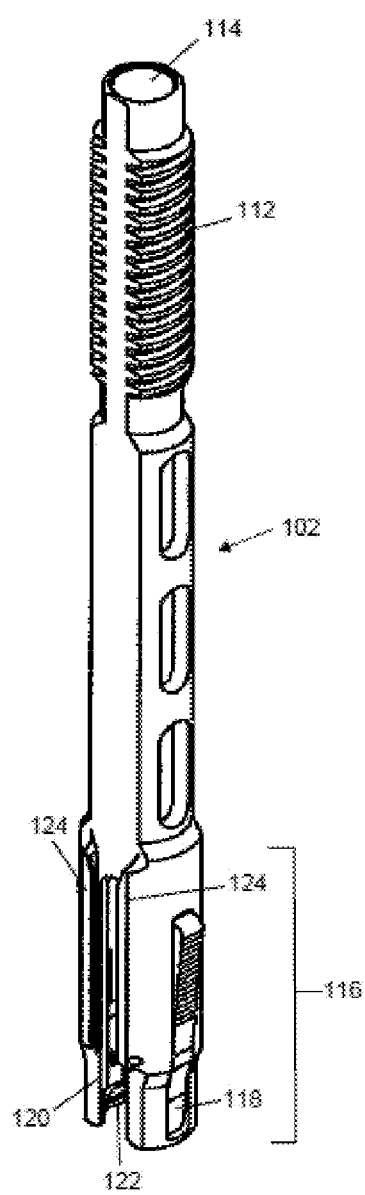
FIG. 5 is a perspective view of a derotation tube of the exemplary instrument according to the principles of the present disclosure.

Continuing now with FIG. 5, the inner member 102 includes a proximal end extendable outside a surgical wound and a distal end for attachment or coupling to the vertebrae. The proximal end may include a threaded portion 112 configured to couple with the outer member 104. A thru-bore 114 extends from the proximal end to the distal end of the inner member 102. The distal end includes a coupling portion 116 for coupling with a spinal implant such as a rod-receiving head of a poly-axial bone screw (not shown). The coupling portion 116 may include an elongated segment having an arcuate cross-section corresponding to the rod-receiving head. A locking member 118, such as a hinged tab, may lock the coupling portion 116 to the spinal implant. The locking member 118 may toggle from a locked position to an unlocked position as the coupling portion 116 advances onto the spinal implant. The locking member 118 may include a projection extending radially inward to engage with mating features on the spinal implant such as a groove or an aperture in the locked position.

A pair of coupling portions 116 may extend from the distal end to form a slot 120 through which the fixation rod may be inserted. The slot 120 may terminate in an opening 122 of the coupling portions 116 at the distal end. A pair of the slots 120 may be formed by the pair of coupling portions 116 on opposite sides of the distal end of the inner member 102. The slot 120 may include a guide portion 124. For example, the guide portion 124 may include a channel or groove in the sidewalls of the slot 120. The guide portion 124 may extend the length of the slot 120 to the opening 122. The guide portion 124 may partially extend radially away from the coupling portion 116 to form a lip or edge around the slot 120.

Figure 6:
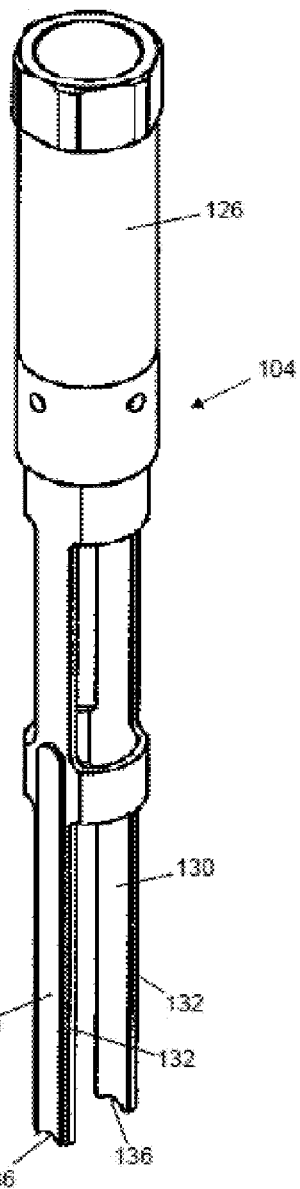
FIG. 6 is a perspective view of a reduction tube of the exemplary instrument according to the principles of the present disclosure.
Figure 10:
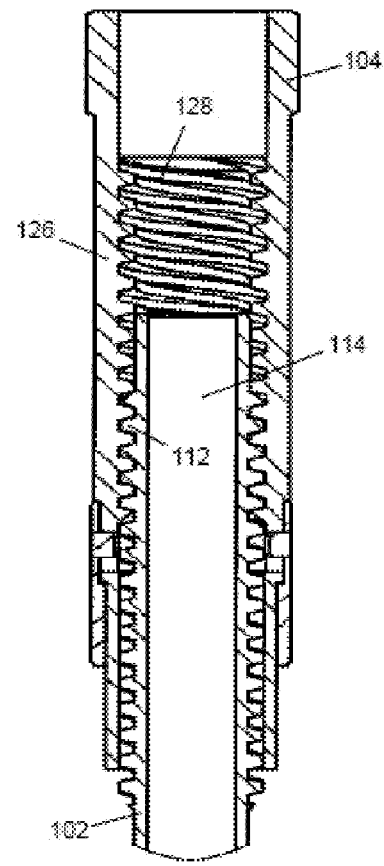
FIG. 10 is a partial cross-sectional view along the plane X of FIG. 7.
Figure 11:
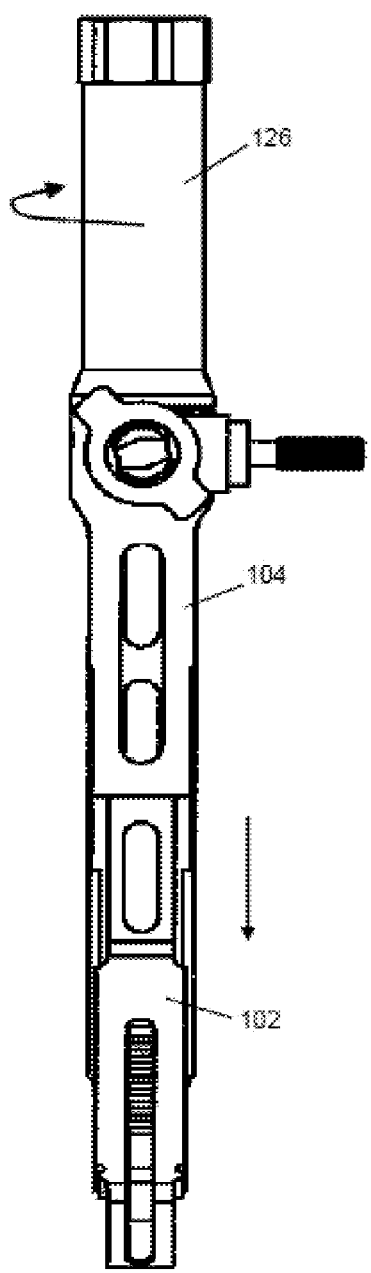
FIGS. 11-12 are elevational side views of the instrument according to the principles of the present disclosure.
Figure 12:
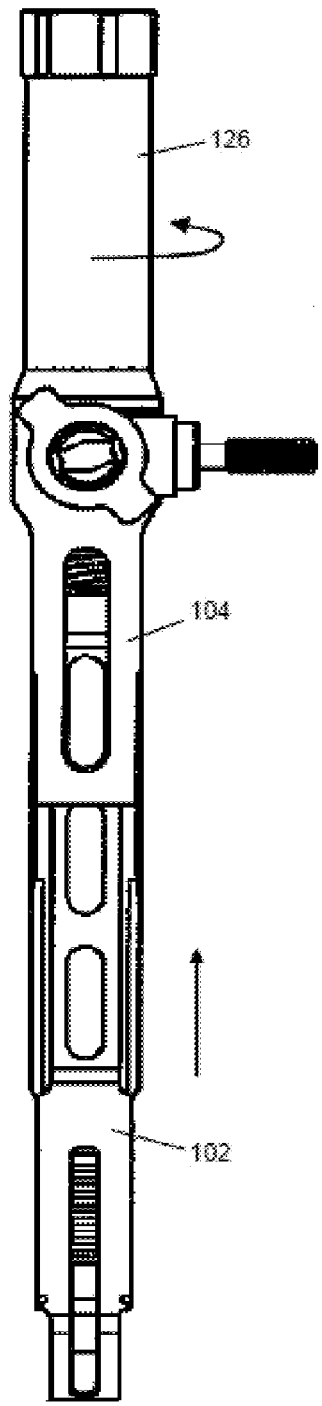
Figure 13:
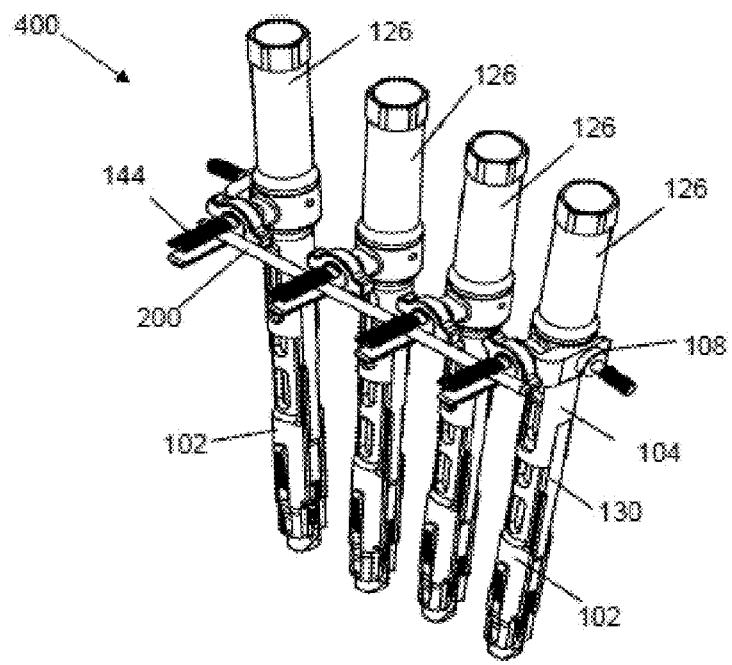
FIGS. 13-14 are perspective views of the system according to the principles of the present disclosure.

Referring now to FIG. 6, the outer member 104 includes a proximal end extendable outside the surgical wound and a distal end for engagement with the fixation rod. The proximal end includes a driving feature 126, such as a rotatable handle, that engages the proximal end of the inner member 102. The driving feature 126 may freely rotate on the proximal end of the outer member 104. Referring now to FIG. 10, the driving feature 126 may include internal threading 128 that engages with the threaded portion 112 of the inner member 102. Rotating the driving feature 126 positions the outer member 104 relative to the inner member 102 along a shared concentric axis L. For example, in FIGS. 11 and 12, the driving feature 126 may rotate in a first direction A to advance the outer member 104 towards the distal end of the inner member 102 in direction B. The driving feature 126 may rotate in an opposite second direction C to retract the outer member 104 away from the distal end of the inner member 102 in direction D.

Figure 7:
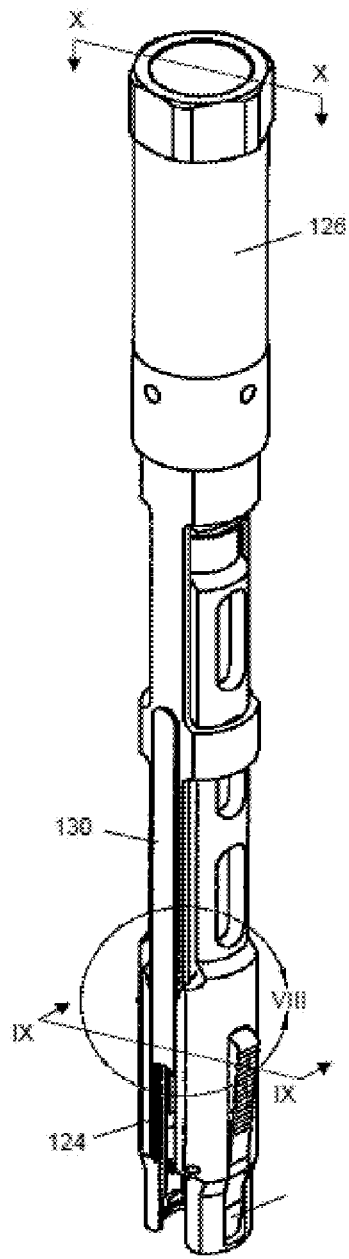
FIG. 7 is a perspective view of the derotation tube and reduction tube in sliding engagement according to the principles of the present disclosure.
Figure 9:
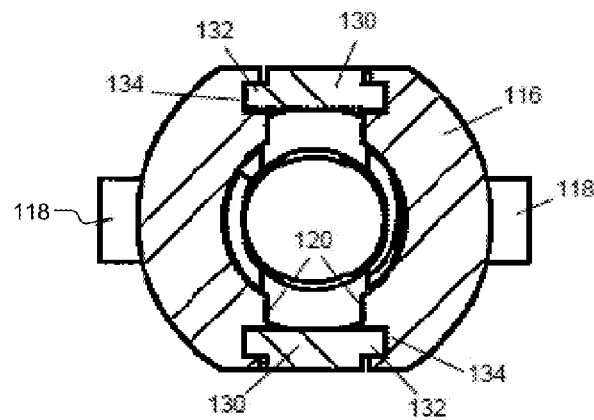
FIG. 9 is a cross-sectional view along the plane IX of FIG. 7.
Figure 8:
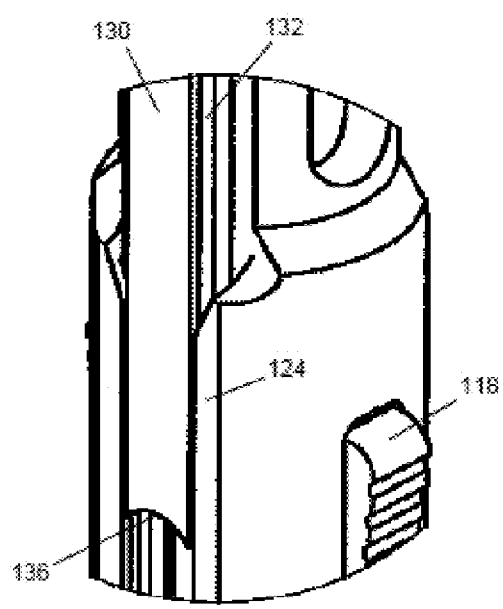
FIG. 8 is a magnified perspective view of the region VIII of FIG. 7.

Continuing with FIG. 6, the distal end of the outer member 104 includes one or more elongated segments or reduction blades 130. Each reduction blade 130 may be configured to slidably engage each guide portion 124 of the slots 120 as shown in FIGS. 7-9. For example, the reduction blade 130 may include a ridge or tongue 132 that engages a channel or groove 134 in the guide portion 124 of the slot 120. A pair of reduction blades 130 may engage the corresponding pair of guide portions 124 in the slots 120. The guide portions 124 may support the reduction blades 130 and prevent inward and outward deflection as the reduction blades 130 apply force to the fixation rod during a rod reduction procedure. The guide portions 124 may align the reduction blades 130 with the slots 120 in a tongue and groove configuration as shown in FIGS. 8 and 9. At the distal end of the reduction blade 130, a rod engagement feature 136, such as a contoured tip, may be configured to contact the fixation rod.

Referring back to FIG. 3, the first coupler 106 may include a rotating coupler configured to receive an alignment rod 200 for aligning multiple instruments 100 in a system 400 as shown in FIGS. 13-16. Linking multiple instruments 100 together allows en bloc rotation and positioning of two or more vertebrae. The first coupler 106 may rotatably couple to the outer member 104 to allow rotation of the alignment rod 200. For example, the outer member 104 may include a bore 138 having an axis that is perpendicular to the axis of the thru-bore 114 of the inner member 102. The bore 138 receives a post 140 extending from the first coupler 106. The bore 138 and post 140 may include threading or other features for selectively locking the first coupler 106 to the outer member 104. A locking nut 142 may lock the first coupler 106 at a desired angle relative to the outer member 104.

Figure 14:
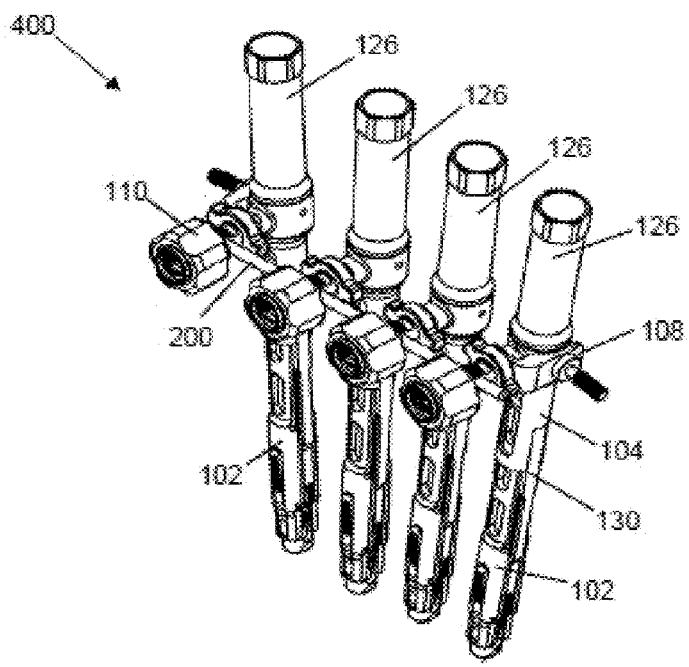

The first coupler 106 may include a slotted receiver 144 that extends away from the outer member 104 in a direction substantially aligned with the axis of the bore 138. The slotted receiver 144 may be configured to receive the alignment rod 200. The slotted receiver 144 may extend away from the locking nut 142 some distance to allow for movement of the alignment rod 200 in multiple directions. For example, in FIG. 13 the alignment rod 200 may be free to move along a length of the slotted receiver 144. That is, the alignment rod 200 may slide within the slotted receiver 144 in a first direction parallel do the axis of the bore 138 and a second direction defined by the desired angle of the first coupler 106. In FIG. 14, the locking knobs 110 may lock the alignment rod 200 within the coupler 106. The locking knobs 110 may also be used to pull an instrument 100 coupled with a misaligned vertebra towards the alignment rod 200 that is rigidly secured against one or more other instruments 100 coupled with properly aligned vertebrae.

Figure 15:
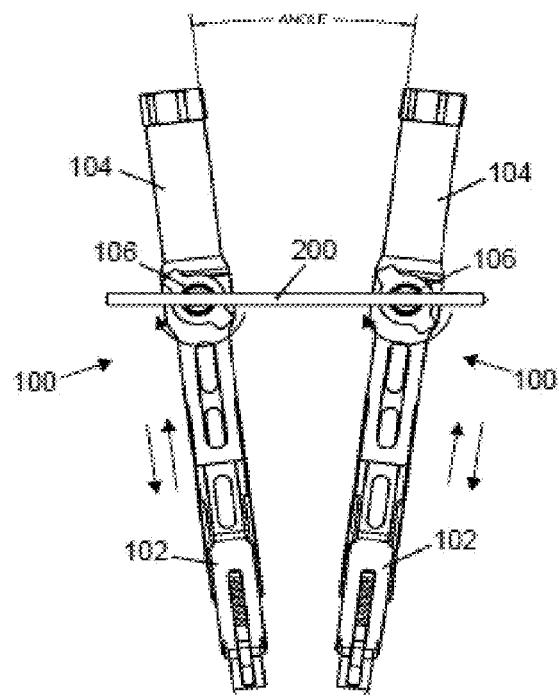
FIGS. 15-16 are elevational side views of the system according to the principles of the present disclosure.
Figure 16:
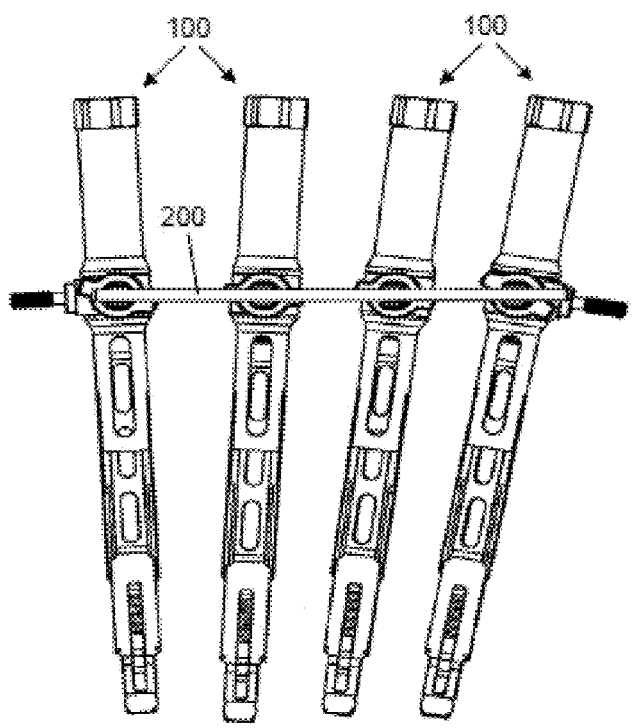

Referring now to FIGS. 15 and 16, a variety of angles between adjacent instruments 100 may be associated with the curvature of the spine. The angles may result from divergent or convergent posterior X axes of each vertebra. In order to link adjacent instruments 100, the couplers 106 on each instrument 100 may be aligned to accommodate for the varying angles. The first coupler 106 and sliding outer member 104 may be adjusted to accommodate varying angles between each vertebra. For example, these angles may be accommodated by rotation of the first coupler 106 and positioning of the outer member 104 relative to the inner member 102. Thus, each coupler 106 rotates axially to accommodate the variable lordotic angle of each vertebra. The reduction tube 104 may be used to position the couplers 106 vertically. Once all the couplers 106 are properly aligned, the alignment rod 200 may be inserted to join all vertebral segments together. The connected vertebrae may then be rotated in unison.

Figure 17:
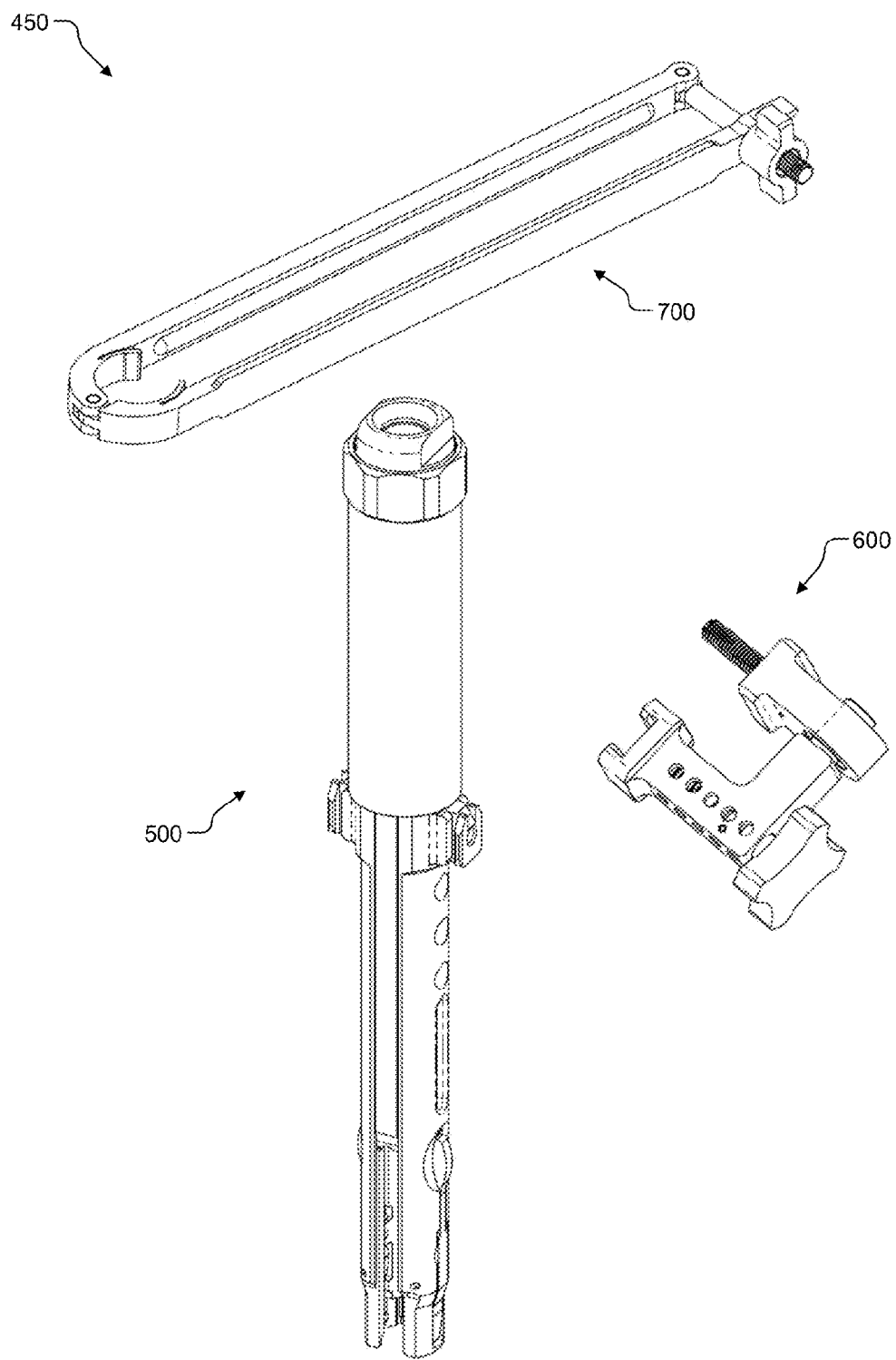
FIG. 17 is a perspective view of another exemplary system for derotation, rod reduction, and alignment of multiple segments of the spinal column according to the principles of the present disclosure.

Continuing now with FIG. 17, another exemplary system 450 includes an instrument 500 with similar features as the prior exemplary instrument 100 and that may be interchangeable with the prior exemplary instrument 100 in system 400. A bracket 600 may include various features for quick attachment and removal from the instrument 500 as well as various features for coupling with alignment rods 200. An alignment clip 700 may clamp around two or more instruments 500 to position them in unison. Similar to the system 400 in FIG. 3, the system 450 may be used to align the vertebrae of the spine.

Figure 18:
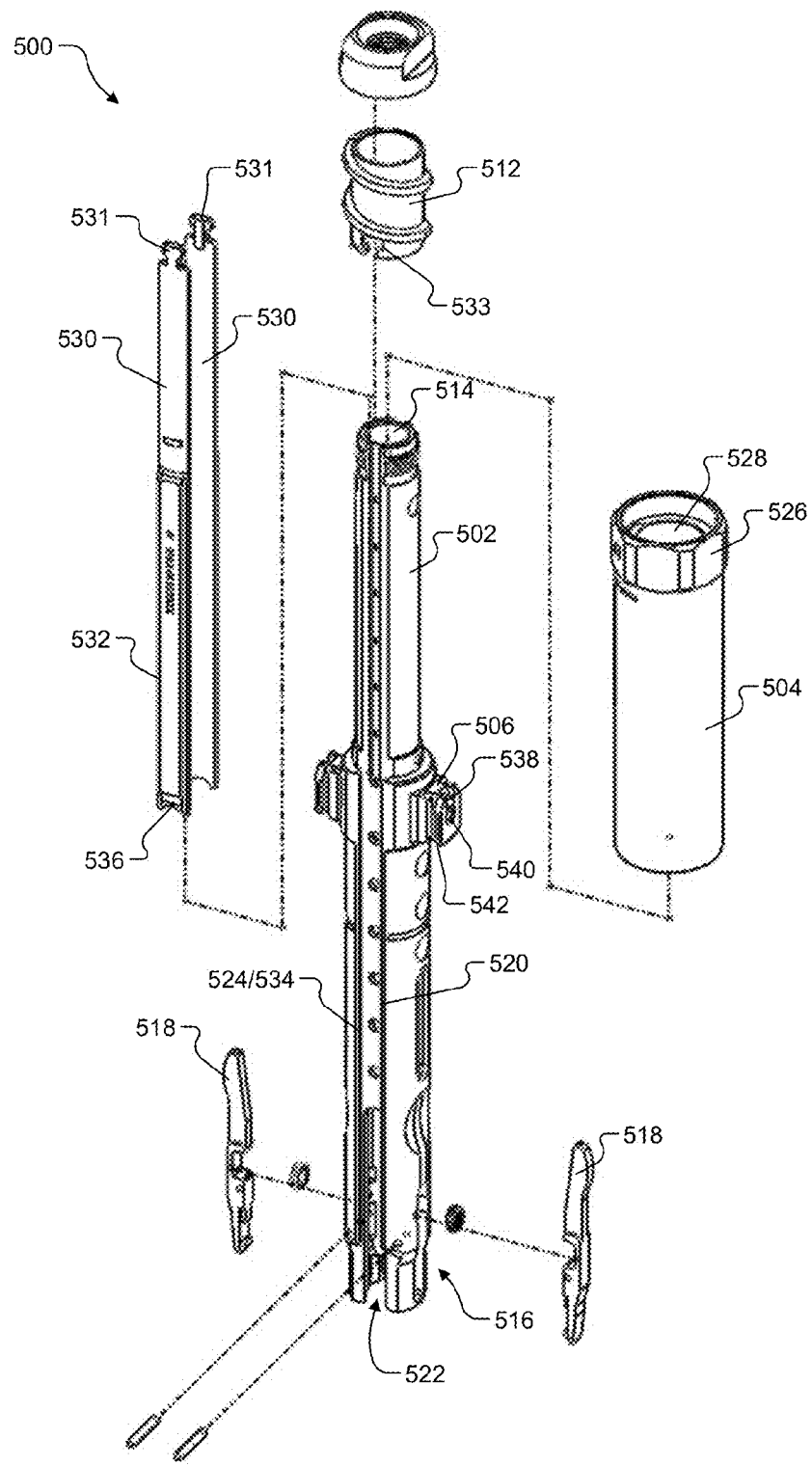
FIG. 18 is an exploded perspective view of another exemplary instrument for derotation, rod reduction, and alignment of the spinal column according to the principles of the present disclosure.

Referring now to FIG. 18, the instrument 500 includes an inner member 502 with a proximal end extendable outside a surgical wound and a distal end for attachment or coupling to a pedicle screw inserted into the vertebra. The proximal end may include a threaded portion 512 configured to couple with an outer member 504 and slide along the inner member 502. The threaded portion 512 may include a sleeve with an external thread and a smooth inner bore. A thru-bore 514 extends from the proximal end to the distal end of the inner member 502.

The distal end includes a coupling portion 516 for coupling with a spinal implant such as a rod receiving head of a poly-axial bone screw (not shown). The coupling portion 516 may include an elongated segment having an arcuate cross-section. A locking member 518, such as a hinged tab, may lock the coupling portion 516 to the spinal implant. The locking member 518 may toggle from a locked position to an unlocked position as the coupling portion 516 advances onto the spinal implant. The locking member 518 may include a projection extending radially inward to engage with mating features on the spinal implant such as a groove or an aperture in the locked position.

A pair of coupling portions 516 may extend from the distal end to form a slot 520 through which the fixation rod may be inserted. The slot 520 may terminate in an opening 522 of the coupling portions 516 at the distal end. A pair of the slots 520 may be formed by the pair of coupling portions 516 on opposite sides of the distal end of the inner member 502. The slot 520 may include a guide portion 524. For example, the guide portion 524 may include a channel or groove in the sidewalls of the inner member 502. The guide portion 524 may extend the length of the slot 520 to the opening 522. The guide portion 524 may partially extend radially away from the coupling portion 516 to form a lip or edge around the slot 520.

The outer member 504 includes a proximal end extendable outside the surgical wound and a distal end for engagement with additional removable features that engage the fixation rod. The proximal end includes a driving feature 526, such as a rotatable handle, that engages the proximal end of the inner member 502. The driving feature 526 may freely rotate on the proximal end of the outer member 504. The driving feature 526 may include internal threading 528 that engages with the threaded portion 512 of the inner member 502. Rotating the driving feature 526 positions the threaded portion 512 along a shared concentric axis L relative to the inner member 502. For example, in FIGS. 19A-19C, the driving feature 526 may rotate in a first direction indicated by arrow A to advance or translate the threaded portion 512 inside of the driving feature 526 towards the distal end of the inner member 502 indicated by arrow B. The driving feature 526 may rotate in an opposite second direction to retract the threaded portion 512 away from the distal end of the inner member 502.

The driving feature 526 may not translate relative to the inner member 502 thus keeping the instrument 500 at a constant overall length. In this respect, the instrument 500 differs from instrument 100. A locking cap 544 may retain the driving feature 526 on the proximal end of the inner member 502. For example, the driving feature 526 may include a retainer ring 546 on a proximal end that engages a ridge 548 of the proximal end of the inner member 502. The locking cap 544 may retain the retainer ring 546 in contact with the ridge 548 by threaded engagement with the proximal end of the inner member 502.

Figures 19A, 19B, 19C:
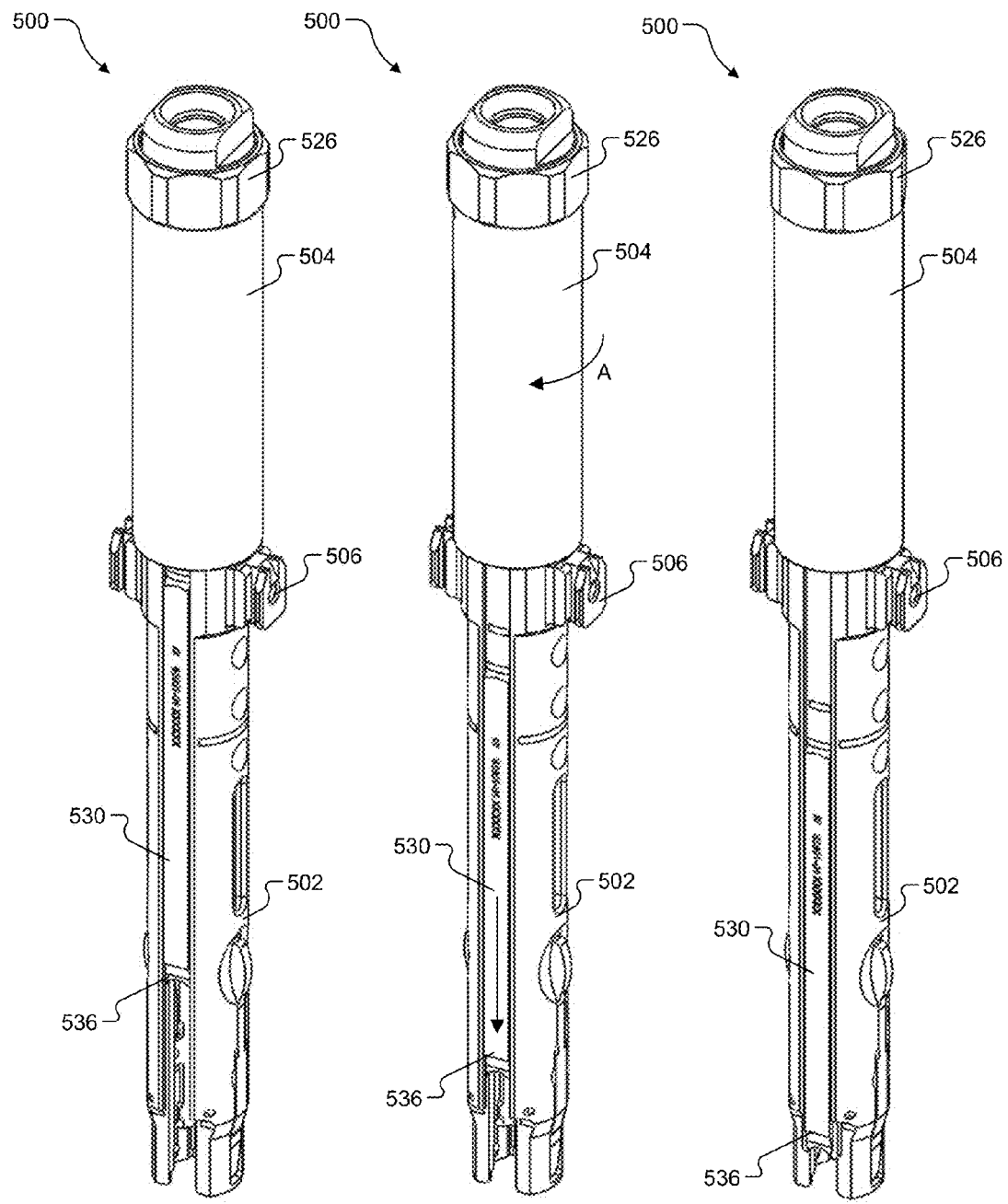
FIGS. 19A-19C are a series of perspective views illustrating application of a reduction force by the exemplary instrument of FIG. 18 according to the principles of the present disclosure.

Continuing with FIG. 18, the instrument 500 may include a pair of removable reduction blades 530. Each reduction blade 530 may be configured to slidably engage each guide portion 524 of the slots 520 as shown in FIGS. 19A-19C. For example, the reduction blade 530 may include a ridge or tongue 532 that engages a channel or groove 534 in the guide portion 524 of the slot 520. A pair of reduction blades 530 may engage the corresponding pair of guide portion 524 in the slots 520. The guide portions 524 may support the reduction blades 530 and prevent inward and outward deflection as the reduction blades 530 apply force to the fixation rod during a rod reduction procedure. The guide portions 524 may align the reduction blades 530 with the slots 520 in a tongue and groove configuration. At the distal end of the reduction blade 530, a rod engagement feature 536, such as a contoured tip, may be configured to contact the fixation rod.

At the proximal end of each reduction blade 530, a tab 531 may project proximally to engage with the threaded portion 512. The tab 531 may include a geometry profile to interlock with the threaded portion 512 such that as the driving feature 526 rotates, the threaded portion 512 may pull the blades 530 proximally or distally along the longitudinal axis of the instrument 500. In FIG. 18, the tabs 531 are depicted as generally dovetailed or T-shaped and engaging with a mating recess 533 of the threaded portion 512. However, any geometry capable of both pushing and pulling the blades 530 within the channel 534 of the guide portion 524 may be used.

Figure 20:
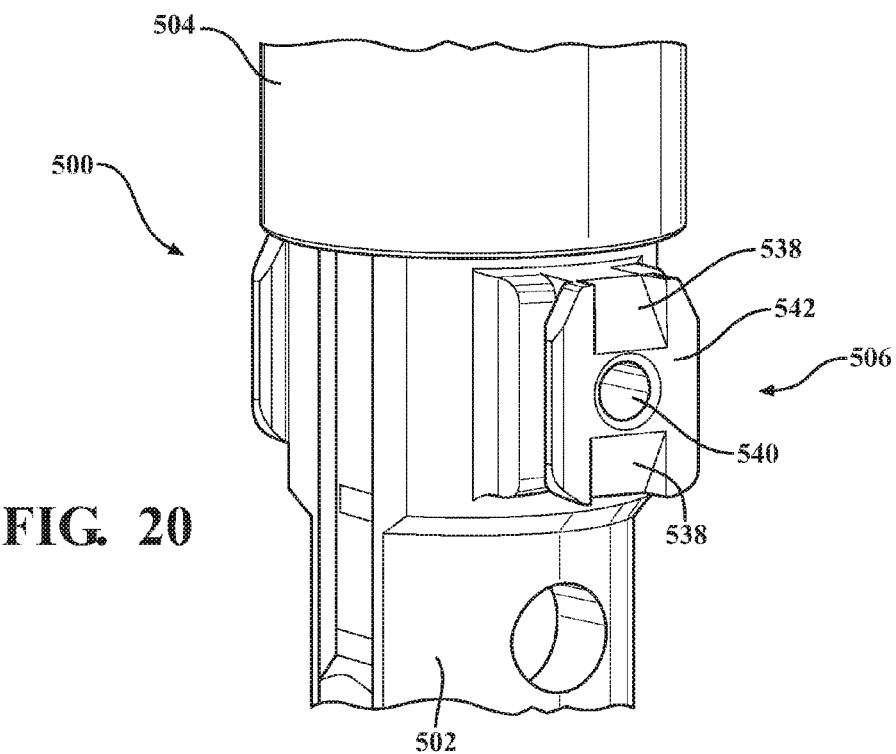
FIG. 20 is an enlarge view of an exemplary mount portion of the instrument according to the principles of the present disclosure.

As shown in greater detail in FIG. 20, the instrument 500 may include multiple coupler mounts for attaching one or more brackets that may receive various crosslinks and alignment members. For example, near the distal end of the outer member 504, the inner member 502 may include a projecting mount 506. The mount 506 may project radially from the inner member 502 and include one or more ramped portions 538 to facilitate a quick connect feature for receiving the brackets 600. The mount 506 may further include a radially extending aperture 540 for receiving the brackets 600. The mount 506 may further include ridges or beveled edges, tongue-and-groove, T-shaped profile, or other configurations 542 that may restrict insertion of the brackets 600 onto the mount 506 in one direction. The projecting mount 506 may be disposed anywhere along the length of the inner member 502.

Figure 22A:
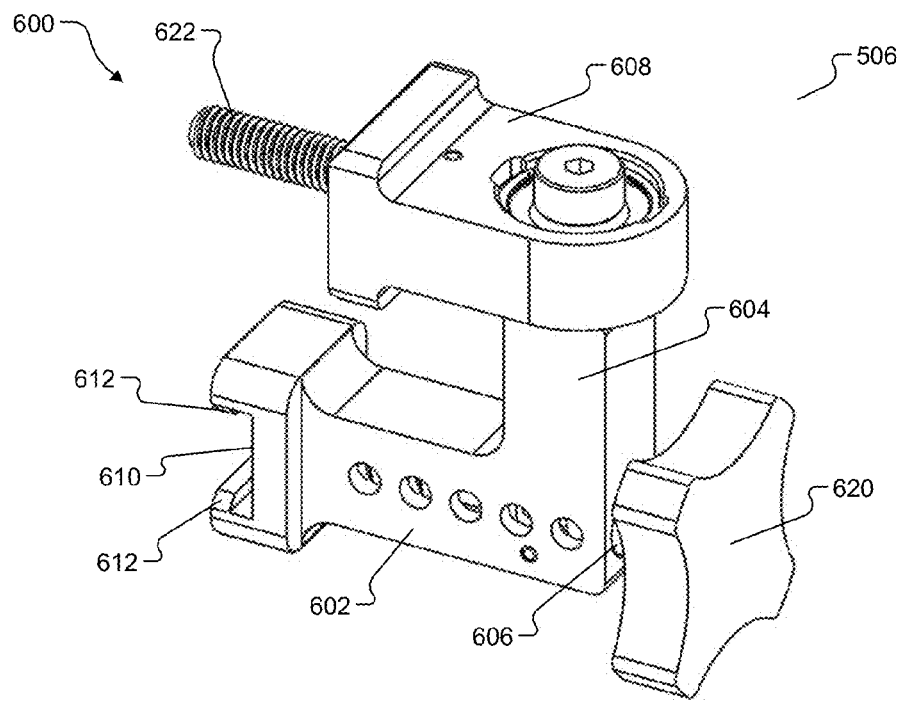
FIGS. 22A and 22B are perspective views of another exemplary bracket for receiving a crosslink according to the principles of the present disclosure.
Figure 22B:
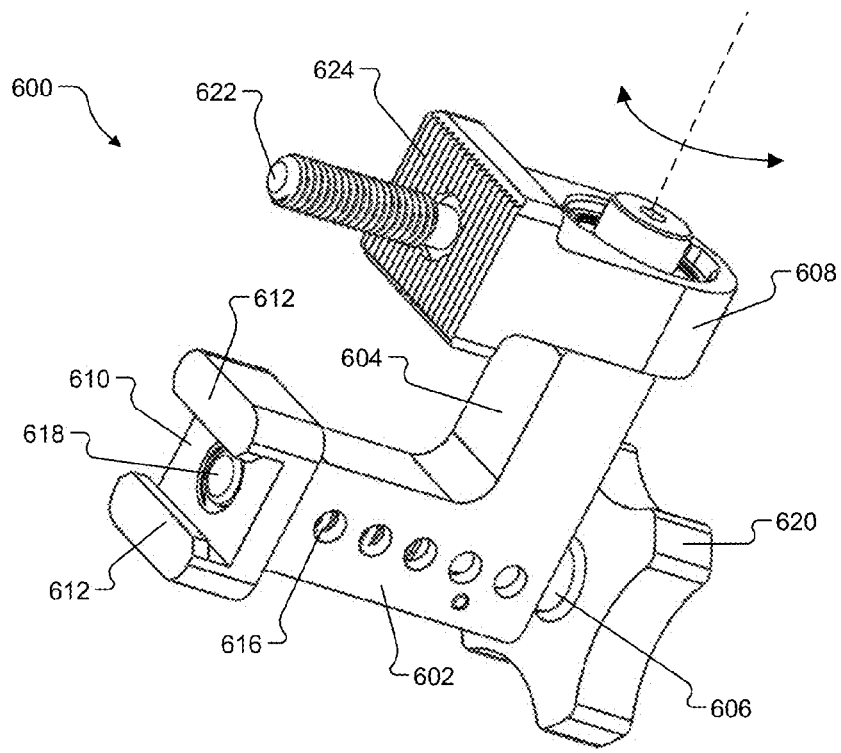
Figure 23:
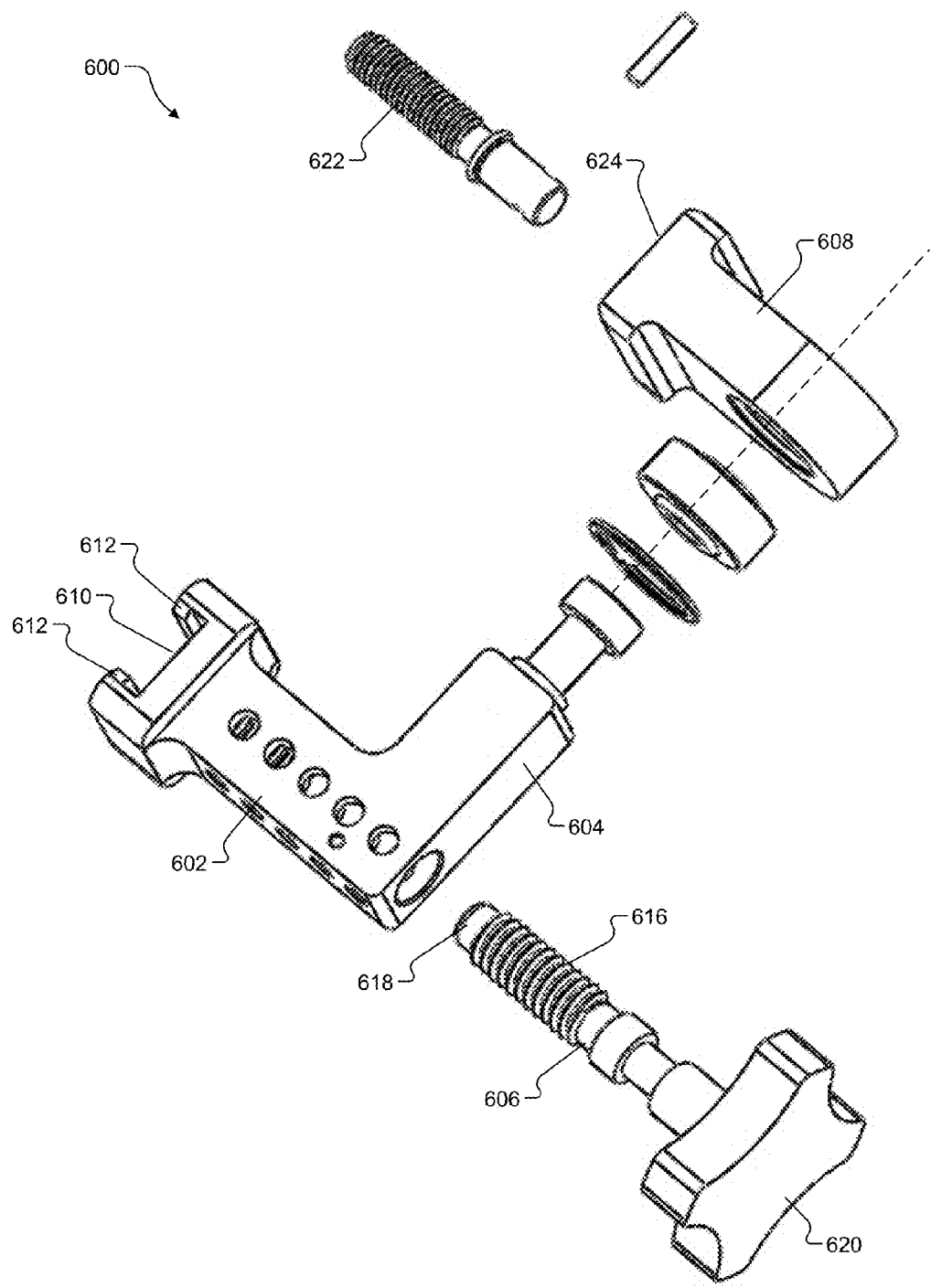
FIG. 23 is an exploded perspective view of the bracket of FIGS. 22A and 22B.

Referring to FIGS. 22A, 22B, and 23, an exemplary bracket 600 includes various features for quick connect to the mount 506 and attachment of crosslinks 300, alignment rods 200, and/or alignment clips 700 to enable en block rotation and alignment of multiple levels of vertebrae. The bracket 600 may include a transverse member 602, a longitudinal member 604, a quick connect pin 606, and a rotatable crosslink connector 608. The transverse member 602 and the longitudinal member 604 may be disposed at a 90 degree angle or at any angle required for a derotation procedure.

The transverse member 602 may be configured to attach to the mount 506. At one end of the transverse member 602, a mating feature 610 may be configured to mate with various features of the mount 506 such as the tongue-and-groove configuration. For example, the mating feature 610 may include a channel 612 with edges 614 extending inwardly towards one another. The channel 612 may slide over the T-shaped mount 506. The pin 606 may include a threaded portion 616 for engagement with threads of the aperture 540 in the mount 506. Alternatively, the pin 606 may be a spring-loaded pin with a tip 618 configured to slide along the ramped portions 538 and "pop" into the aperture 540. A knob 620 on an opposite end of the pin 606 from the tip 618 may facilitate grasping and/or rotation of the pin 606 to insert or remove the bracket 600 from the mount 506.

The rotatable member 608 may rotate about a longitudinal axis passing through longitudinal member 604. The rotatable member 608 may include a threaded post 622 to receive one or more alignment rods and/or crosslinks. For example, the crosslink 300 may be secured to the threaded post 622 by a threaded knob similar to the knob 110 of FIG. 3. The rotatable member 608 may include a textured surface 624 to prevent a crosslink 300 from slipping during a derotation and alignment procedure.

Figure 21:
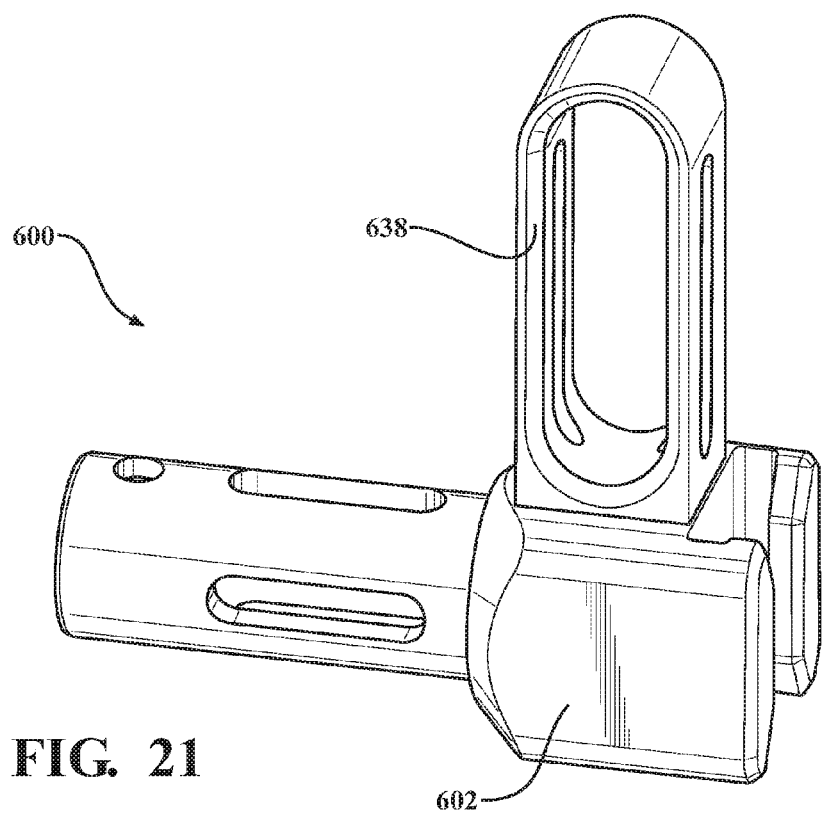
FIG. 21 is a perspective view of an exemplary bracket for receiving a crosslink according to the principles of the present disclosure.

Referring to FIG. 21, a bracket 900 may include various features and shapes to accommodate connection of multiple linkages between adjacent towers of a single vertebral level or spanning multiple vertebral levels for en bloc derotation and/or alignment. In FIG. 21, the bracket 600 includes a slotted connection 638.

Figure 24A:
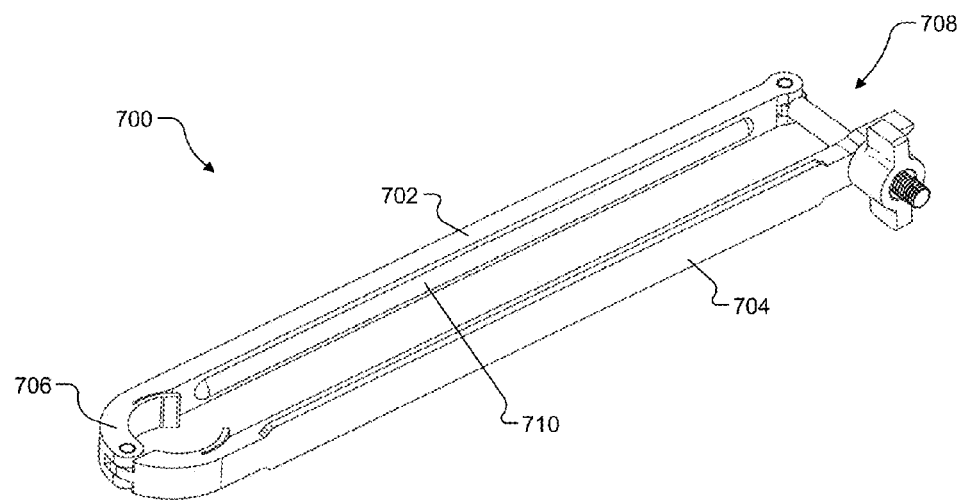
FIGS. 24A and 24B are perspective views of an exemplary alignment clip according to the principles of the present disclosure.
Figure 24B:
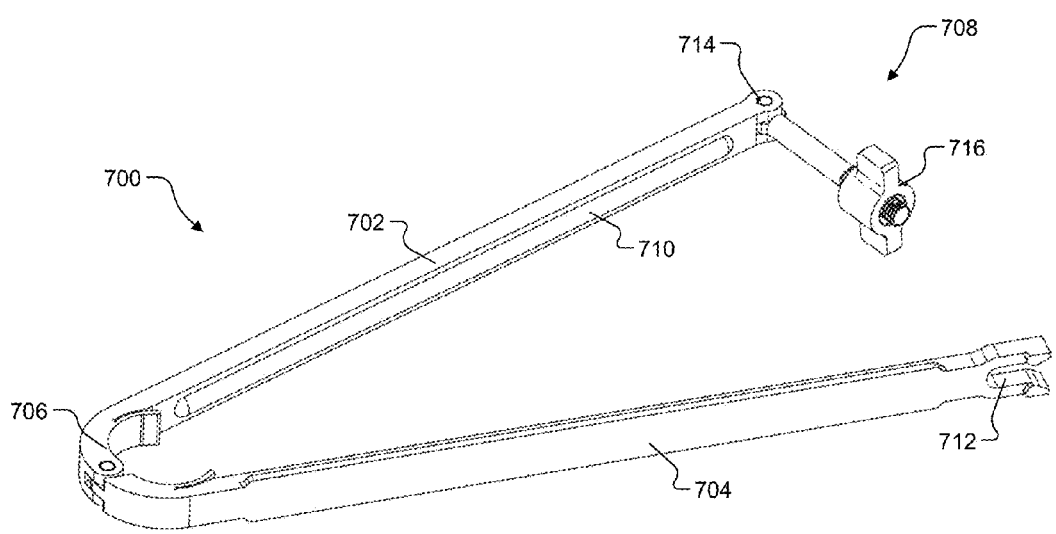

Referring to FIGS. 24A and 24B, the alignment clip 700 includes a pair of elongate arms 702 and 704, a hinge 706 at a first end, and a locking mechanism 708 at a second end. Along an inner-facing surface of each arm, a gripping portion 710, such as a rubber or silicone-based strip, may be provided to grasp the instruments 400. The hinge 706 may be spring loaded. The locking mechanism 708 may include a clasp 712 on an end of one arm 704 and a pin 714 on an end of the other arm 702. A nut 716 may be used to secure the pin 714 within the clasp 712. At the first end, the arms 702 and 704 may form a circular portion 718 configured to grasp one of the instruments 500.

Referring now to FIGS. 25-29, additional components for use with the instruments 100 and 500 are shown that enable connection of an alignment rod 200 along the length of the spine. For example, in FIGS. 25-29, a bracket 800 may include a locking mechanism 630 to lock the pin 606 in place once the bracket 800 is attached to the mount 506. The locking mechanism 630 may include a lever 632 attached to a threaded rod 834. As the lever 632 rotates, the threaded rod 634 engages the pin 606. In addition, the pin 606 may be coupled with a spring 636 that biases the pin 606 towards the channel 610 and mount 506. Thus, the bracket 800 may be attached to the mount 506 by sliding the channel 610 over the mating features of the mount 506. The end 618 may slide along the ramped portions 538 of the mount 506 forcing the pin 606 away from the mount 506. As the end 618 of pin 606 reaches the aperture 540, the spring 634 force the pin 606 into the aperture 540 for a quick snap-fit.

Figure 25:
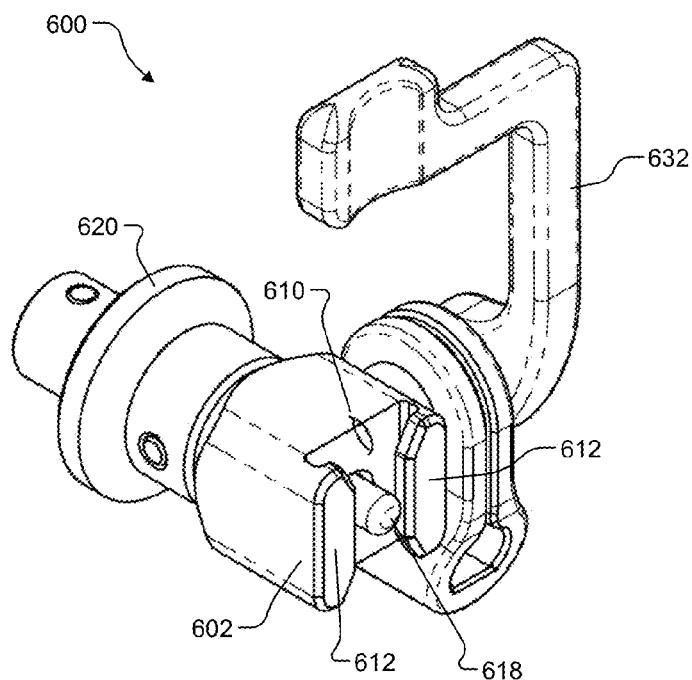
FIGS. 25 and 26 are perspective views of another exemplary bracket for receiving a crosslink and/or an alignment rod according to the principles of the present disclosure.
Figure 26:
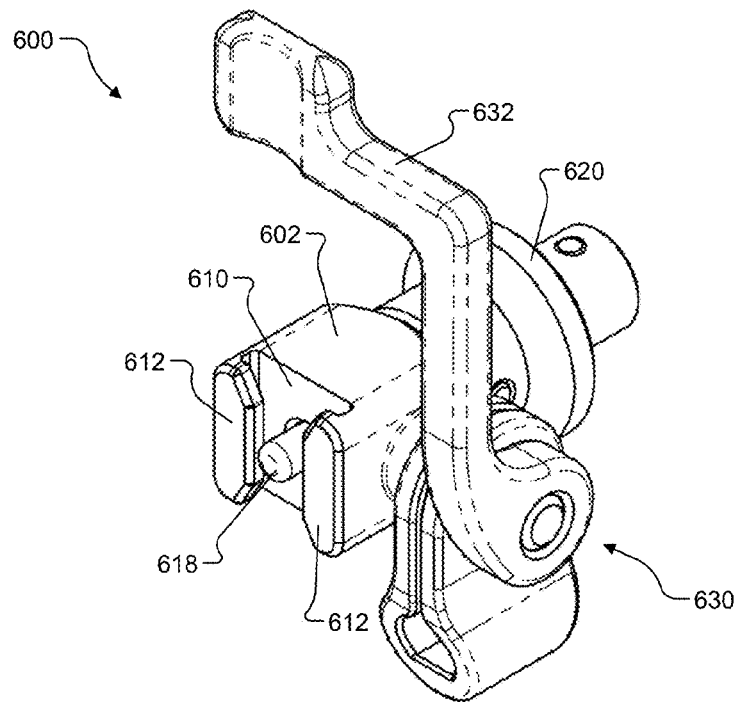
Figure 27:
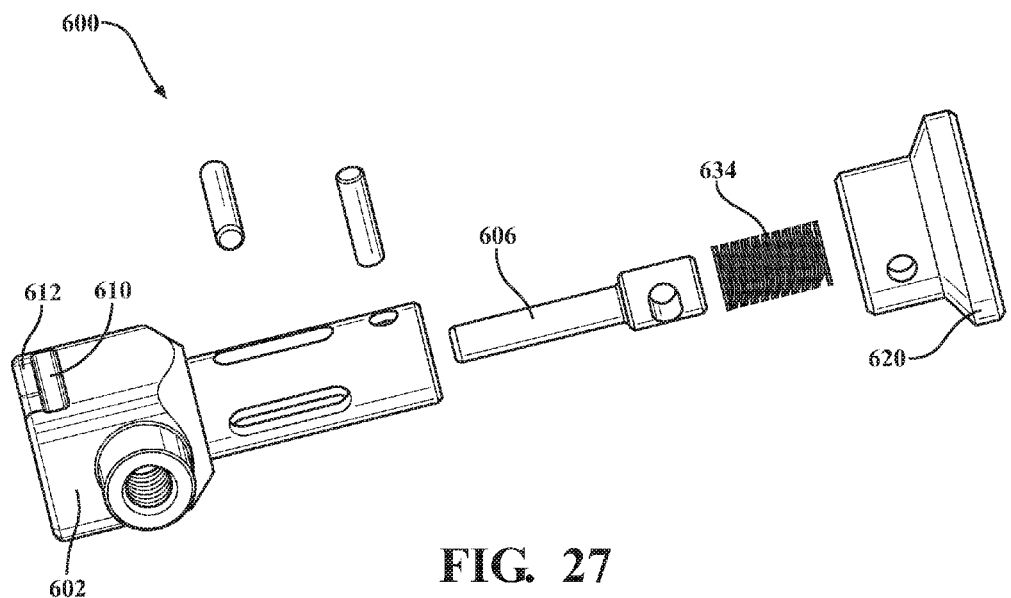
FIG. 27 is an exploded view of a portion of the bracket of FIGS. 25 and 26.
Figure 28:
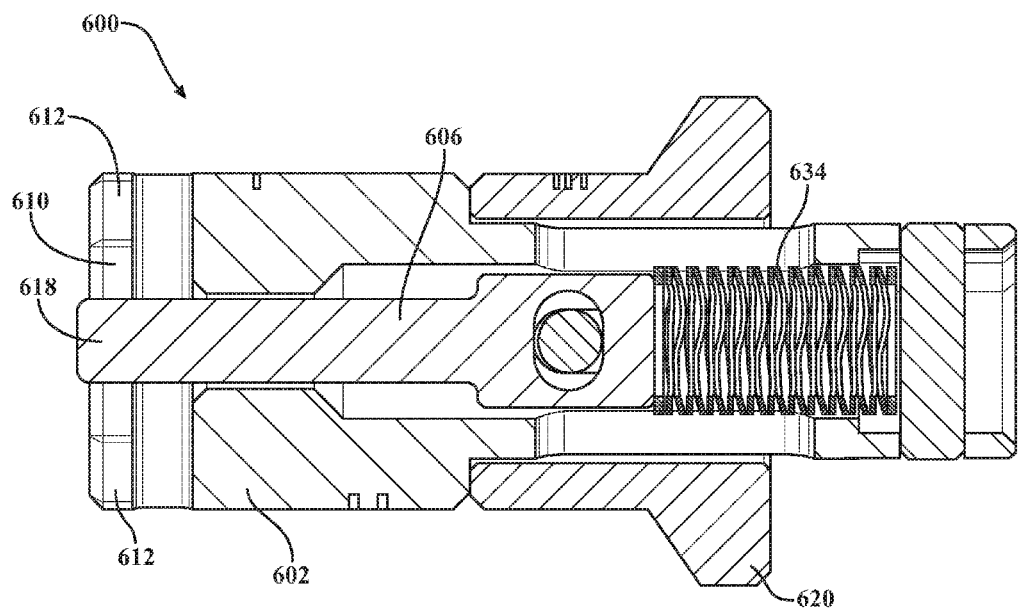
FIG. 28 is a cross-sectional view of the bracket of FIG. 27.
Figure 29:
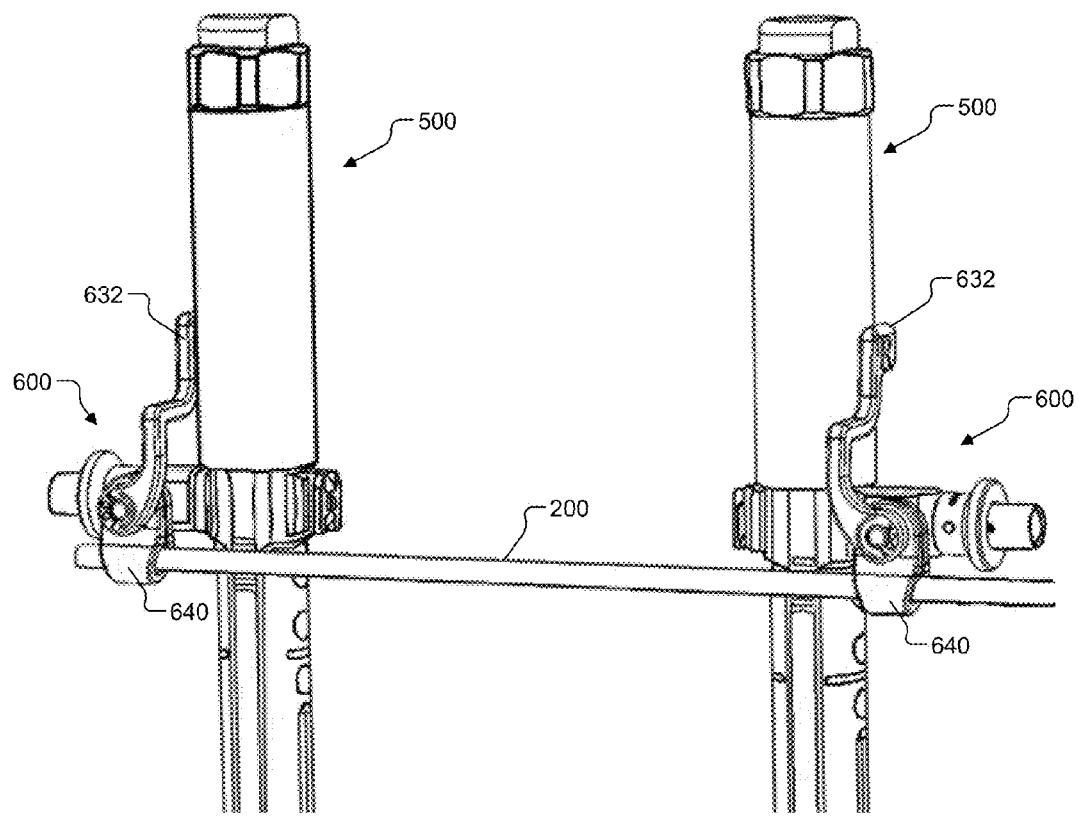
FIG. 29 is a perspective view of components of exemplary systems for derotation, rod reduction, and alignment of multiple segments of the spinal column according to the principles of the present disclosure.

Referring to FIGS. 25, 26, and 29, the bracket 600 may include clips 640 to receive the alignment rod 200. The clips 640 may be banded clips including a compressible end 642 and a receiving end 644. In some examples, the receiving end 644 may be configured to receive a cylindrical alignment rod 200. In other examples, the receiving end 644 may be configured to receive a D-shaped alignment rod 200 having one flat surface. The compressible ends 642 of the clips 640 may be coupled with the locking mechanism 630 such that when the lever 632 rotates to lock the brackets 600 to the mounts 506, the threaded rod 634 pulls the lever 632 to compress the compressible end 642 of the clip 640. As the force on the compressible end 642 increases with rotation of the lever 632, the clips 640 grasp the alignment rod 200 more tightly to secure the entire construct with one action.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. An instrument for correction of spinal deformities and rod reduction, comprising:
   an inner member including a proximal portion configured to receive a corrective force and a distal coupling portion configured to transfer the corrective force to a spinal implant in a vertebra;
   a slot extending transversely through the coupling portion and configured to guide a fixation rod into the spinal implant;
   a threaded sleeve including an external thread and a thru-bore that slides relative to the proximal portion of the inner member;
   an outer member coupled with the proximal portion of the inner member and engaged with the external thread to apply a reduction force to the threaded sleeve as the outer member rotates relative to the inner member; and a reduction blade having a pair of longitudinally extending edges, each of the pair of longitudinally extending edges extending the length of the blade, each of the pair of longitudinally extending edges spaced apart from each other whereby the reduction blade only partially extends around the threaded sleeve, the reduction blade including a proximal interlocking portion that removably couples with the threaded sleeve and a distal rod engagement feature configured to engage the fixation rod and transfer the reduction force to reduce the fixation rod into the spinal implant.

2. The instrument of claim 1, further comprising a second reduction blade including a proximal interlocking portion that removably couples with the threaded sleeve and a distal rod engagement feature configured to engage the fixation rod and transfer the reduction force to reduce the fixation rod into the spinal implant.

3. The instrument of claim 1, further comprising a guide portion of the inner member aligned with the slot and configured to prevent deflection as the reduction blade applies the reduction force.

4. The instrument of claim 3, wherein the guide portion and the reduction blade engage in a tongue-and-groove configuration.

5. The instrument of claim 3, wherein engagement between the reduction blade and the guide portion prevents rotation of the threaded sleeve relative to the inner member.

6. The instrument of claim 1, wherein the distal coupling portion comprises a locking member including a hinged tab with a projection extending radially inward to engage a recess of the spinal implant.

7. The instrument of claim 1, further comprising a mount projecting from the inner member configured to receive a bracket.

8. The instrument of claim 7, wherein the mount includes include one or more ramped portions, a radially extending aperture, and one or more of ridges, beveled edges, a tongue-and-groove, and a T-shaped profile that restricts insertion of the bracket to one direction.

9. The instrument of claim 7 wherein the bracket is configured to couple the instrument with a second instrument on an opposite side of the vertebra by a crosslink.

10. The instrument of claim 9, wherein the bracket comprises:
a transverse member extending from the mount and including a pin to engage the mount;
a longitudinal member extending from the transverse member at a 90 degree angle; and
a rotatable member on an end of the longitudinal member that includes a post to receive the crosslink.

11. The instrument of claim 10, wherein the pin includes a threaded portion and the mount includes a threaded aperture, wherein the pin locks the bracket to the mount by threaded engagement.

12. The instrument of claim 10, wherein the pin includes a spring-loaded pin and the mount includes an aperture, wherein the pin is biased into the aperture to lock the bracket to the mount.

13. The instrument of claim 1, wherein the outer member includes a retainer ring that engages a ridge of the proximal portion to prevent linear translation of the outer member relative to the inner member.

14. The instrument of claim 1, wherein the proximal interlocking portion comprises a T-shaped projection that couples with a mating T-shaped recess of the threaded sleeve.

15. A system for linking two spinal implants inserted in a one vertebra to share corrective
forces applied to the vertebra and reduce two rods into the spinal implants, comprising:
first and second instruments, each instrument including
an inner member including a proximal portion with a mount configured to receive a corrective force and a distal coupling portion configured to transfer a portion of the corrective force to a spinal implant in a vertebra;
a slot extending transversely through the coupling portion and configured to guide a fixation rod into the spinal implant;
a threaded sleeve including an external thread and a thru-bore that slides relative to the proximal portion of the inner member;
an outer member coupled with the proximal portion of the inner member and engaged with the external thread to apply a reduction force to the threaded sleeve as the outer member rotates relative to the inner member; and
a reduction blade having a pair of longitudinally extending edges, each of the pair of longitudinally extending edges extending the length of the blade, each of the pair of longitudinally extending edges spaced apart from each other whereby the reduction blade only partially extends around the threaded sleeve, the reduction blade including a proximal interlocking portion that removably couples with
the threaded sleeve and a distal rod engagement feature configured to engage the fixation rod and transfer the reduction force to reduce the fixation rod into the spinal implant;
first and second brackets coupled with the first and second instruments respectively, each bracket including a transverse member extending from the mount and including a pin to engage the mount;
a longitudinal member extending from the transverse member at a 90 degree angle; and
a rotatable member on an end of the longitudinal member that includes a post to receive a crosslink;
a cross link coupled to each post of the first and second brackets that transfers a portion of the corrective force applied to the first instrument to the second instrument.

16. A system for linking two spinal implants inserted in two different vertebrae to share corrective forces applied to the vertebrae and reduce a rod into the spinal implants, comprising
first and second instruments, each instrument including an inner member including a proximal portion with a mount configured to receive a corrective force and a distal coupling portion configured to transfer the corrective force to a spinal implant in a vertebra;
a slot extending transversely through the coupling portion and configured to guide a fixation rod into the spinal implant;
a threaded sleeve including an external thread and a thru-bore that slides relative to the proximal portion of the inner member;
an outer member coupled with the proximal portion of the inner member and engaged with the external thread to apply a reduction force to the threaded sleeve as the outer member rotates relative to the inner member; and a reduction blade, whereby the reduction blade only partially extends around the threaded sleeve, including a proximal interlocking portion that removably couples with the threaded sleeve and a distal rod engagement feature configured to engage the fixation rod and transfer the reduction force to reduce the fixation rod into the spinal implant, the reduction blade extending the length of the slot so as to at least partially cover the slot; and an alignment clip configured to couple the first and second instruments to enable en bloc positioning of the vertebrae.

17. The system of claim 16, wherein the alignment clip comprises:

a first arm and a second arm;

a hinge portion at a first end of the first and second arms pivotably couples the first arm to the second arm; and a locking portion at a second end of the first and second arms locks the first arm to the second arm.

18. The system of claim 17, wherein the hinge portion forms a circular portion configured to couple with the outer member of one of the first and second instruments.

19. The system of claim 17, wherein the locking portion comprises a pin on the first arm, a clasp on the second arm, and a nut to retain the pin in the clasp.

20. The system of claim 17, wherein the first arm and second arm each includes a gripping portion comprising one of a rubber and a silicone-based material to grip one of the first and second instruments.

* * * * *